(12) United States Patent
Poland et al.

(10) Patent No.: US 7,141,020 B2
(45) Date of Patent: Nov. 28, 2006

(54) PORTABLE 3D ULTRASOUND SYSTEM

(75) Inventors: Mckee D Poland, Andover, MA (US); Martha G. Wilson, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/080,160

(22) Filed: Feb. 20, 2002

(65) Prior Publication Data

US 2003/0158482 A1 Aug. 21, 2003

(51) Int. Cl.
*A61B 8/02* (2006.01)

(52) U.S. Cl. .................. 600/447; 600/437; 600/444

(58) Field of Classification Search .............. 600/437, 600/445, 446–449, 441, 459, 463
See application file for complete search history.

(56) References Cited

U.S. PATENT DOCUMENTS

| 5,590,658 | A | * | 1/1997 | Chiang et al. | 600/447 |
| 5,720,289 | A | * | 2/1998 | Wright et al. | 600/443 |
| 5,722,412 | A | * | 3/1998 | Pflugrath et al. | 600/459 |
| 6,013,032 | A | | 1/2000 | Savord | 600/443 |
| 6,102,860 | A | * | 8/2000 | Mooney | 600/443 |
| 6,126,602 | A | | 10/2000 | Savord et al. | 600/447 |
| 6,135,961 | A | | 10/2000 | Pflugrath et al. | 600/447 |
| 6,375,617 | B1 | | 4/2002 | Fraser | 600/443 |

\* cited by examiner

*Primary Examiner*—Brian L. Casler
*Assistant Examiner*—William Jung

(57) ABSTRACT

A portable 3D ultrasound device having an ultrasound transducer. The ultrasound transducer includes a transducer array with a plurality of transducer elements arranged in a plurality of dimensions, the transducer array including an emitter to emit ultrasound energy, a receiver to receive responses generated in accordance with the ultrasound energy, a plurality of sub-array beamformers, a signal processor to convert the generated responses into a 3D ultrasound image and a display unit to display the 3D ultrasound image.

19 Claims, 10 Drawing Sheets

PORTABLE 3D ULTRASOUND SYSTEM

BACKGROUND OF THE INVENTION

1. Field of the Invention

The present invention relates to a portable ultrasound device, and more particularly, to a hand-held or hand-carried ultrasound device that displays a 3D image.

2. Description of the Related Art

Previously, in order to generate a 3D ultrasound image, large machines were required. These machines used transducers having a 1D array of elements, which required complicated circuitry and a complex rocking or back-and-forth movement of the transducer to generate the 3D image. Due to their size and complexity, these machines required large power supplies and heavy power cords, which made these machines even less portable. Furthermore, these machines have not utilized recent advances in computer technology, which allow complex signal processing to be achieved with small chip components. Thus, previous 3D ultrasound machines were either completely stationary, moveable on a cart which weighed 300–400 pounds, or fitted into a large case which was transported in a vehicle trunk, but were too heavy to be carried by hand. These machines were expensive to build and operate, and due to their size, ultrasound analysis could only be performed in certain locations. Although previous portable ultrasound devices were able to generate a 2D image, the circuitry necessary to perform the beamforming, rendering and other processing necessary to generate a 3D image was too large to allow for portability.

SUMMARY OF THE INVENTION

The present invention relates to an apparatus comprising a portable ultrasound device, comprising an emitter to emit ultrasound energy, a receiver to receive responses generated in accordance with the emitted ultrasound energy, a signal processor to convert the generated responses into a 3D ultrasound image, and a display unit to display the 3D ultrasound image.

The present invention further relates to an apparatus comprising a portable ultrasound device, comprising a transducer, comprising a plurality of acoustic elements to transmit ultrasound energy and receive responses generated in accordance with the ultrasound energy, and a plurality of sub-array beamformers to generate a plurality of sub-array summed acoustic signals from the generated responses; a dynamic beamformer, comprising a plurality of dynamic receive delays to delay the sub-array summed acoustic signals, and a full-array summer to sum the delayed sub-array summed acoustic signals to generate a full set of beamformed data; an image detector to generate 3D detected data from the full set of beamformed data; a scan converter to convert the 3D detected data into a 3D ultrasound image; and a display unit to display the 3D ultrasound image.

The present invention further relates to a method comprising scanning a body with a portable or hand-held device; transmitting ultrasound energy from the portable or hand-held device; receiving responses generated in accordance with the transmitted ultrasound energy with the portable or hand-held device; converting the responses to a 3D ultrasound image with the portable or hand-held device; and displaying the 3D ultrasound image on the portable or hand-held device.

BRIEF DESCRIPTION OF THE DRAWINGS

Advantages of the invention will become apparent and more readily appreciated from the following description of the preferred embodiments, taken in conjunction with the accompanying drawings, of which.

DETAILED DESCRIPTION OF THE PREFERRED EMBODIMENTS

Figure 1:
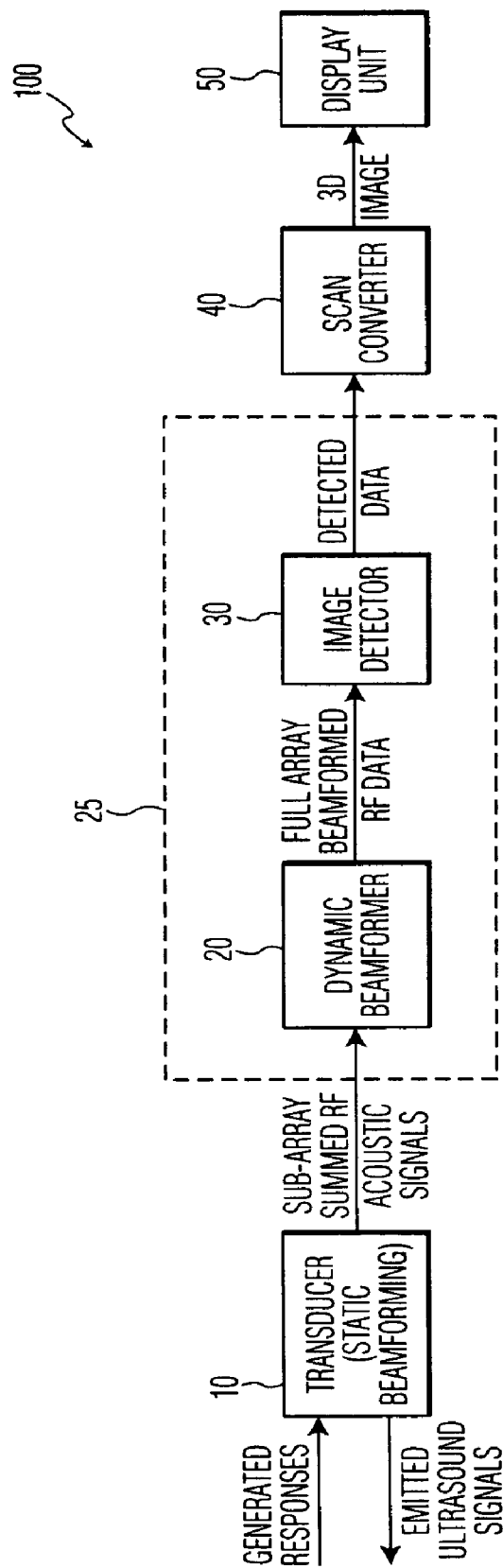
FIG. 1 is a block diagram illustrating the operation of a portable 3D ultrasound device according to the present invention.

Reference will now be made in detail to the present preferred embodiments of the present invention, examples of which are illustrated in the accompanying drawings, wherein like reference numerals refer to like elements throughout.

FIG. 1 is a block diagram illustrating the operation of a portable 3D ultrasound device 100 according to the present invention, which includes hand carry, hand use, or hand-held devices. A transducer 10 emits ultrasound signals which generate a response from a body (not shown) back to the transducer 10. The transducer 10 also provides static beamforming to generate a plurality of sub-array summed RF acoustic signals, which are received by a dynamic beamformer 20. The dynamic beamformer 20 performs dynamic beamforming to generate a full array of beamformed RF data, which is received by an image detector 30, which generates detected acoustic data therefrom. The dynamic beamformer 20 and the image detector 30 are formed on a PC (personal computer) card 25. A scan converter 40 converts the detected acoustic data into a 3D image that is displayed on a display unit 50.

Figure 2A:
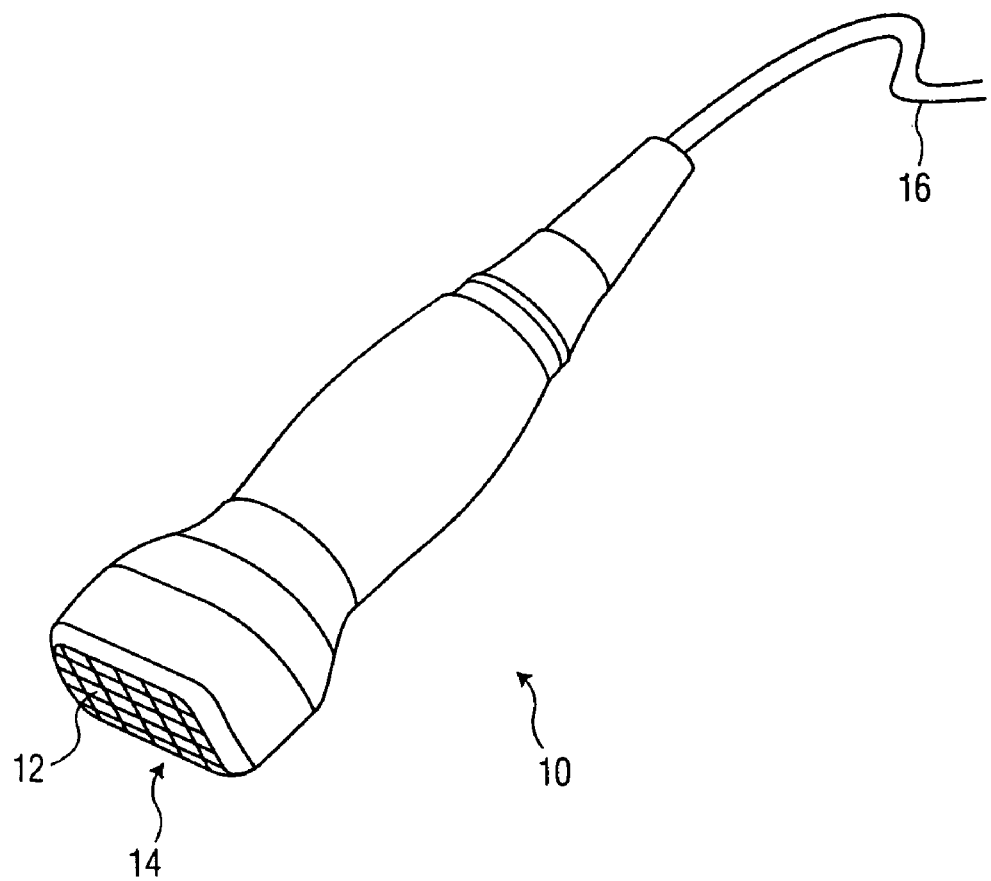
FIG. 2A is a perspective view of the transducer of FIG. 1, according to the present invention.
Figure 2B:
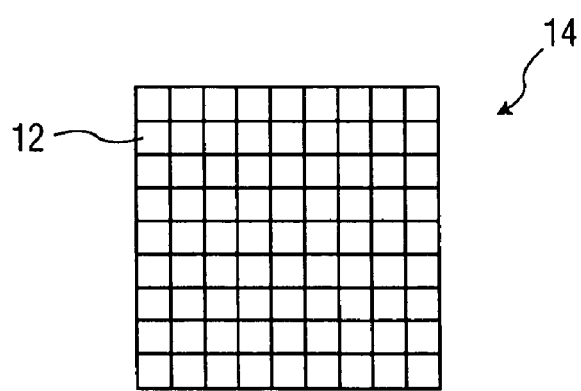
FIG. 2B is an illustration of the 2D array of FIG. 2A, according to the present invention.

FIG. 2A is a perspective view of the transducer 10 of FIG. 1. The transducer 10 are formed on a plurality of acoustic elements 12 arranged in a 2D array 14, and a probe cable 16. The acoustic elements 12 transmit the ultrasound signals and receive the generated responses. FIG. 2B is a top view of the 2D array 14 of FIG. 2A, which comprises between 1000 and 6000 of the acoustic elements 12. As an example, a transducer 10 having approximately 3000 of the acoustic elements 12 will be described. The 2D array 14 is shown as a square matrix in FIG. 2B. However, different shapes such as a rectangular, curved, oval, or circular array, may also be used, and which is optimal depends mainly on the object being analyzed.

Figure 3:
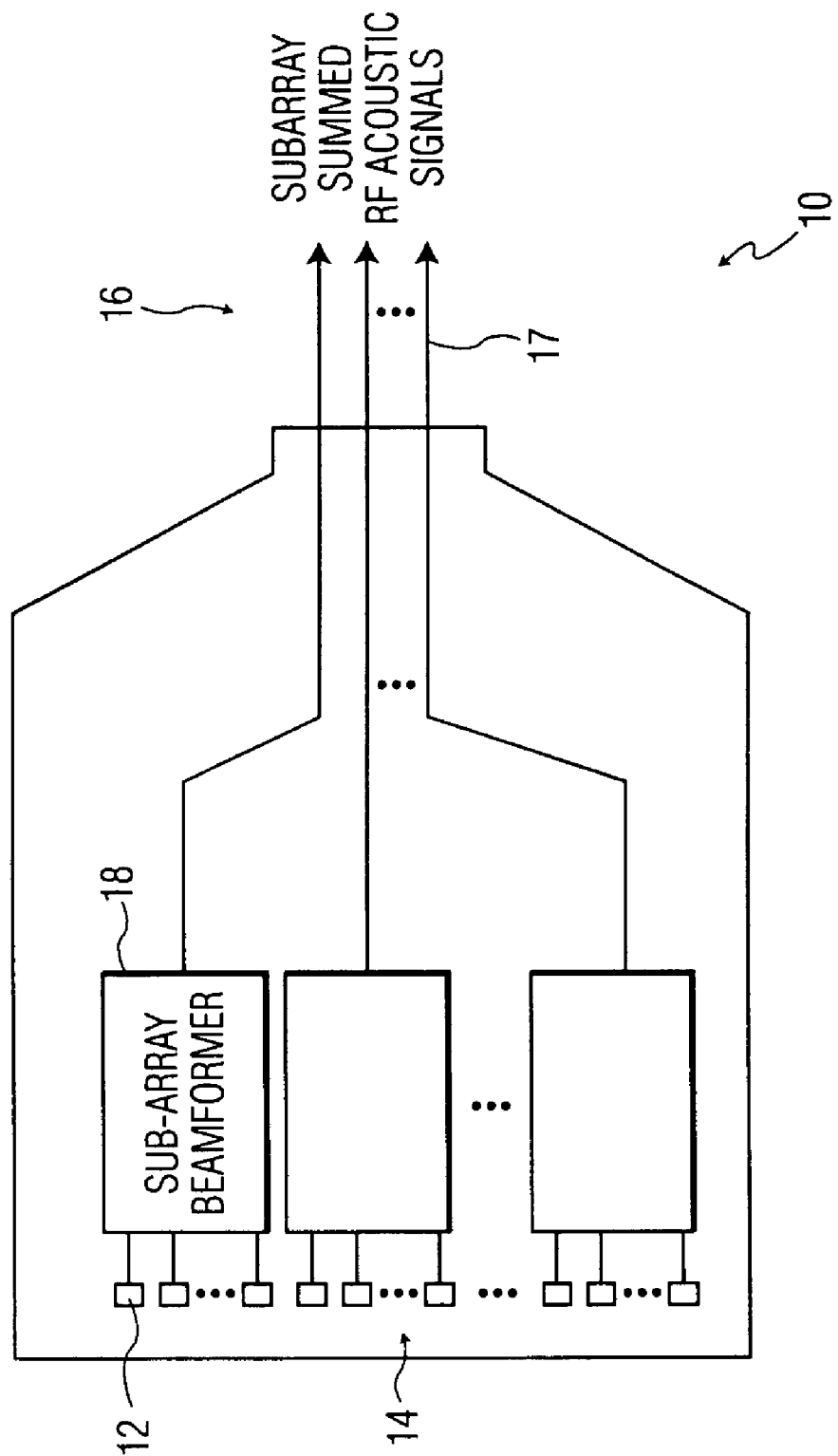
FIG. 3 is a block diagram of the transducer of FIGS. 1, 2A and 2B, according to the present invention.

FIG. 3 is a block diagram of the transducer 10 of FIGS. 1, 2A and 2B. The transducer 10 is comprised of a plurality of sub-array beamformers 18, which control both transmission and reception of acoustic pulses through elements 12, and combine the acoustic responses generated by the scanned medium in order to form the sub-array summed RF acoustic signals, which are then transferred from the transducer 10 through signal lines 17. Each signal line emanates from one sub-array beamformer 18. The signal lines 17 are grouped together inside the probe cable 16. In the present example, there are 128 signal lines 17. Note that not all of the sub-array beamformers 18 need to be connected to the cable 16. Some sub-arrays may be used solely to transmit but not receive, thereby increasing the transmit aperture of the transducer 10 without increasing the number of signal lines 17.

Figure 4:
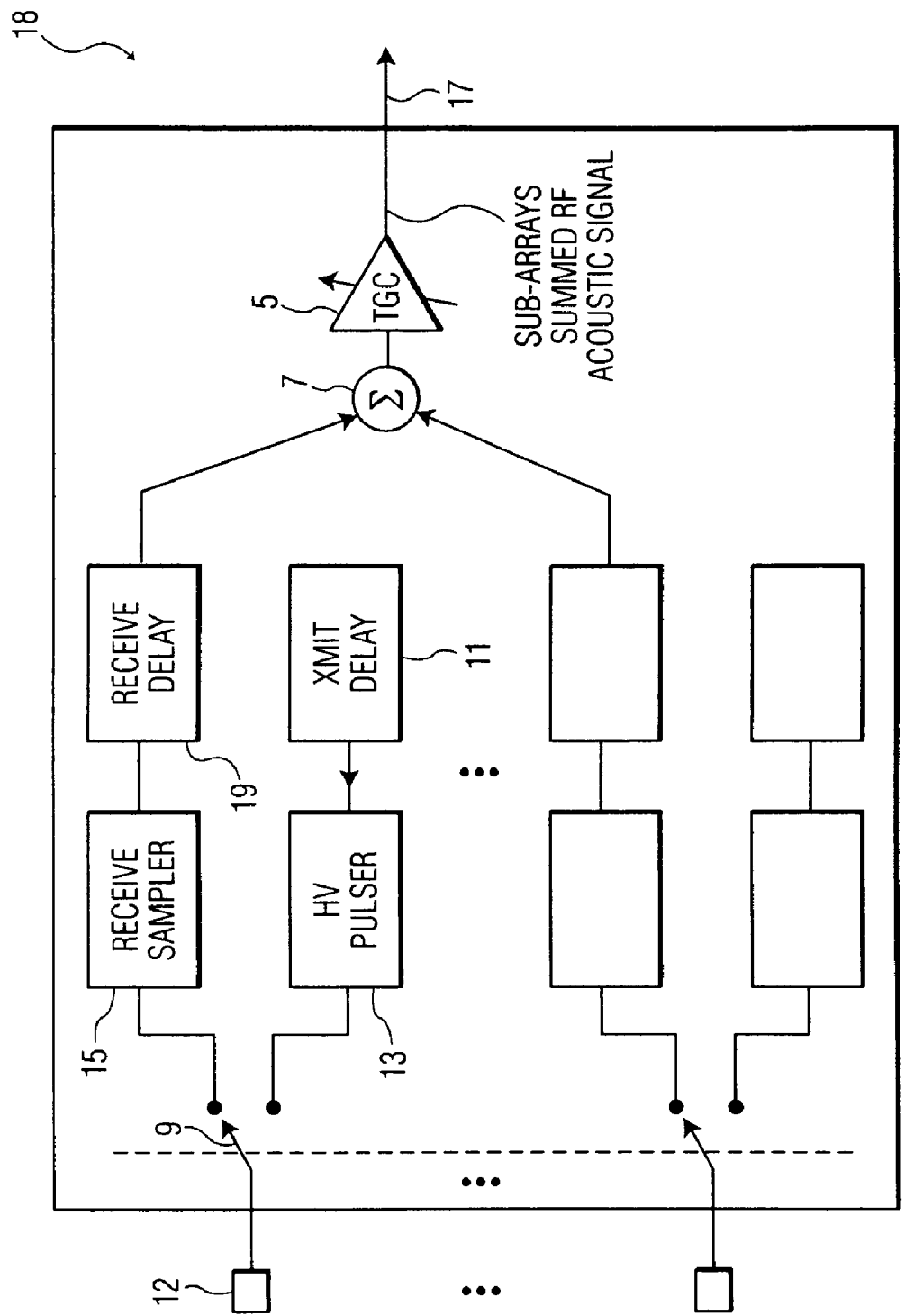
FIG. 4 is a block diagram of the sub-array beamformers of FIG. 3, according to the present invention.

FIG. 4 is a block diagram of the sub-array beamformers 18 of FIG. 3. There are two main phases of beamforming, namely, transmit and receive. During transmit, acoustic pulses are generated from elements 12 of the transducer 10. During the receive phase, echoes from those pulses in the scanned medium are received by elements 12 of the transducer 10, amplified, and combined. For beamforming in the transmit phase, transmit delays 11 and HV (high voltage) pursers 13 generate delayed high voltage pulses. The delayed high voltage pulses go to TIR (transmit/receive) switches 9, which are shown in a receive position in FIG. 4, but would be connected to the HV pulsers 13 at the time of signal transmission. Not shown in FIG. 4 are controls to set individual transmit delays and set voltages of the transmit delays 11 and the HV pulsers 13. Acoustic pulses are transmitted by the acoustic elements 12. The acoustic pulses are timed relative to each other to generate a focus out in space.

In the receive phase, the acoustic pulses previously transmitted are echoed by structures in the body. Between the time that the acoustic pulses are transmitted and the generated pulses are received by the acoustic elements 12, the T/R switches 9 switch to the receive position. Acoustic pulses are received by the acoustic elements 12 from many points on the body, and receive samplers 15 take periodic samples of the resulting acoustic wave to generate analog samples, which are small voltages. The analog samples are then delayed by receive delays 19. The receive delays 19 are static delays, meaning they are unchanged during the course of acoustic reception. The receive delays 19 may also be programmable.

The separately delayed received signals are summed together by first summers 7, and after summing, variable gain amplifiers 5 perform TGC (time gain compensation). Variable gain is required because the signals received by the acoustic elements 12 from later and later times correspond to deeper and deeper depths of the body, and are therefore attenuated. The variable gain amplifiers 5 compensate for this attenuation by increasing output. The sub-array summed RF acoustic signals are transmitted by the signal lines 17.

Figure 5:
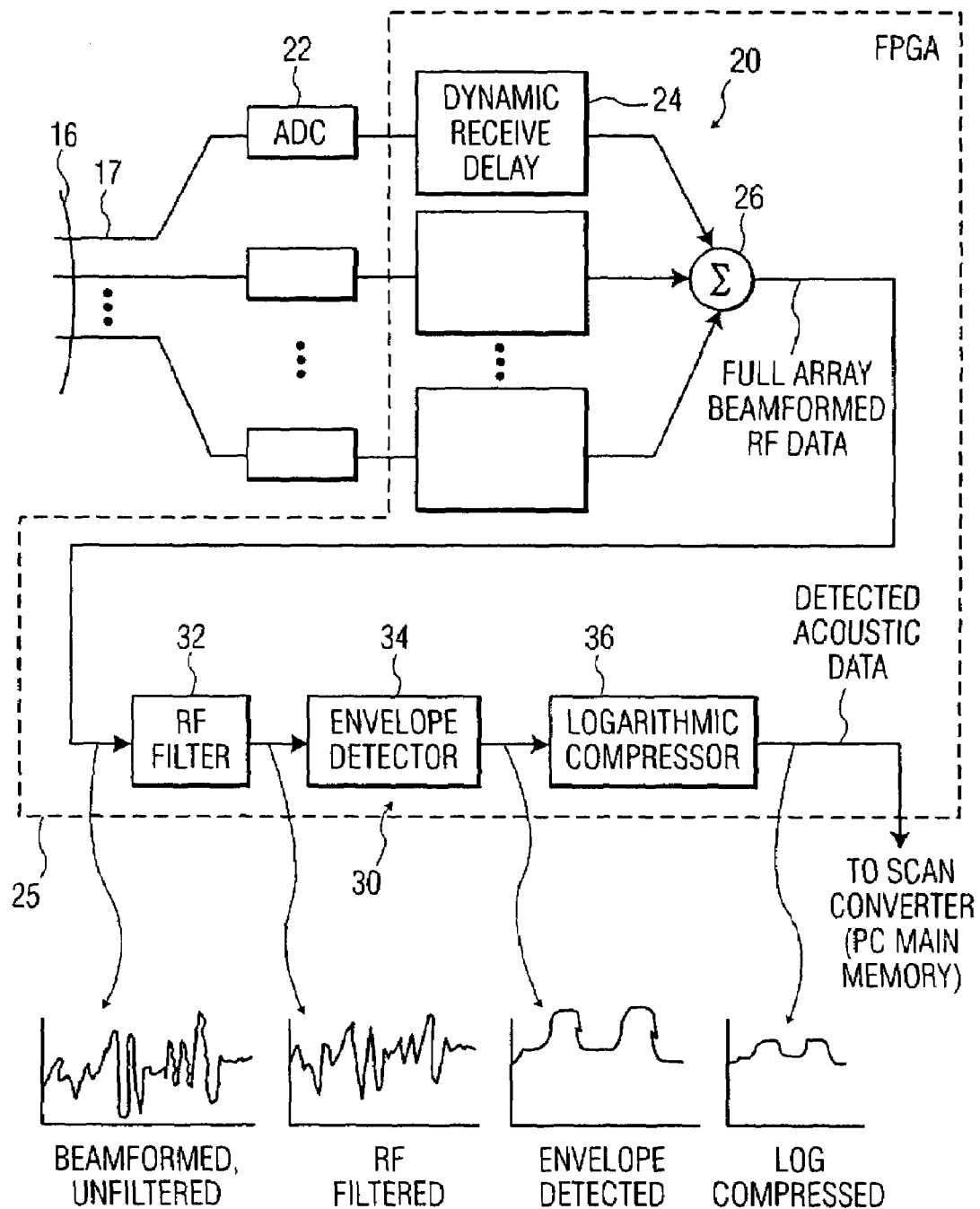
FIG. 5 is a block diagram of the PC card of FIG. 1, according to the present invention, and the waveforms generated therein.

FIG. 5 is a block diagram of the PC card 25 of FIG. 1, and the waveforms generated therein, which comprises the dynamic beamformer 20, which is an FPGA (Field Programmable Gate Array) and the image detector 30. The sub-array summed RF acoustic signals are transmitted to ADC (analog to digital) converters 22, which are on the PC card 25, where they are converted to a stream of digital words. The ADCs 22 have input clocking that clocks at a rate of 10 MHz to generate 10 megabits per second of sub-array beamformed data, which flows into the dynamic beamformer 20 comprising dynamic receive delays 24. Dynamic receive beamforming adjusts the delays of the digital signal samples from ADCs 22 during the entire period of reception of the acoustic echoes. As a result of the repeated delay adjustments, the acoustic focus of the transducer element array is moved along the line formed by the echoes generated by reflections in the scanned medium. The dynamic delays are pre-determined in order to follow the path of the echoes as they propagate through the medium toward the face of the transducer 10, thereby maximizing the resolution of the detected signal at every point. This contrasts with the static beamforming performed on sub-array element groups, because those delays are held constant and thus maximize focus resolution at only a single depth in the echo path. Whereas static delays may preferably be implemented with analog circuitry such as series of sample and hold amplifiers, the dynamic receive delays 24 are digital, and they further delay the sub-array beamformed received signals and adjust each overall delay relative to neighboring signals to improve focus. After being delayed by the dynamic receive delays 24, all of the sub-array beamformed signals are summed into a single full set of beamformed RF data by a second summer 26.

The full set of beamformed RF data is received by the image detector 30, which comprises an RF filter 32, which may be an FIR (finite impulse response) filter. The RF filter 32 suppresses portions of the received signal that are not likely to have originated from the intended transmit waveform, and isolates frequencies in the received signal that provide the most resolution of tissue structures upon detection. The RF filtered signal at the output of filter 32 still contains the transmit carrier frequency, but is modulated in amplitude by the reflections from the scanned tissue structures. The filtered signal passes to an envelope detector 34, which generates a more slowly varying signal that follows the maximum extents, or the envelope, of the fast moving RF filtered signal. The envelope detected signal represents only the intensity of received echoes, with the transmit carrier frequency and other frequencies generated by the acoustic propagation removed. Since echoes are formed in the scanned medium at boundaries between tissues and fluids of different acoustic impedances, the envelope detected signal has relatively high intensities at those boundaries, and can be used by the scan converter and display hardware and software to form a displayable image of the tissues and fluid boundaries themselves. The image detector 30 also comprises a logarithmic compressor 36 to reduce a dynamic range of the envelope detected signals to a range that can be processed by the human eye. This is necessary because the numerical amplitude of the echoes before logarithmic compression is expanded as compared to similar signals seen or heard in nature.

Acoustic detected data is output by the image detector 30, and is then scan converted from polar coordinates into a 3D Cartesian grid by the scan converter 40, which may be a PC consisting at least of a CPU and main memory. After scan conversion and rendering (not shown), the 3D image is generated and displayed by the display unit 50. The rendering may be performed by the PC main memory using rendering algorithms such as Sheer Warp, 3D Texture Mapping and Ray Casting. Due to recent developments in the computer field, PC hardware is now powerful enough and small enough to perform these rendering algorithms and scan conversion in a portable system.

The detected data comprises a 3D volume as measured over time. This 3D volume is made possible by the use of the acoustic elements 12 arranged in the 2D array 14, and by delaying the transmission and reception of the signals to and from each element individually, as described previously. Specifically, the static transmit delays 11 and static receive delays 19 combine with the programming of the dynamic receive delays 24 and together determine the direction of the acoustic scan lines, which may generate and receive echoes along a line oriented in 3D space (through the scanned medium). By scanning multiple lines through 3D space, the set of 3D image data is generated, which is then processed by known 3D rendering methods to form a 3D display of the scanned structures. Thus, the 3D image can be generated in a portable or hand-held ultrasound apparatus, and the transducer 10 need not be rocked or moved back and forth. The 3D image may be a bi-plane (two images of the same object from different angles simultaneously displayed), multiplane (multiple images of the same object at different depths), volumetric (a pyramid of data is displayed, with some of the data being transparent), holographic, or several planes may be scanned, with a selected plane or alternatively, a surface with a user-selected shape, being opaque.

Furthermore, the 3D image is displayed in real time. By real time it is meant that it appears from the point of view of a user that the image represents the actual condition of a patient at every instant in time, even though it may take a very small but finite amount of time for the system to process the information and display the same. Thus, as far as the user can detect, the ultrasound image is contemporaneously displaying the object being analyzed.

Figure 6:
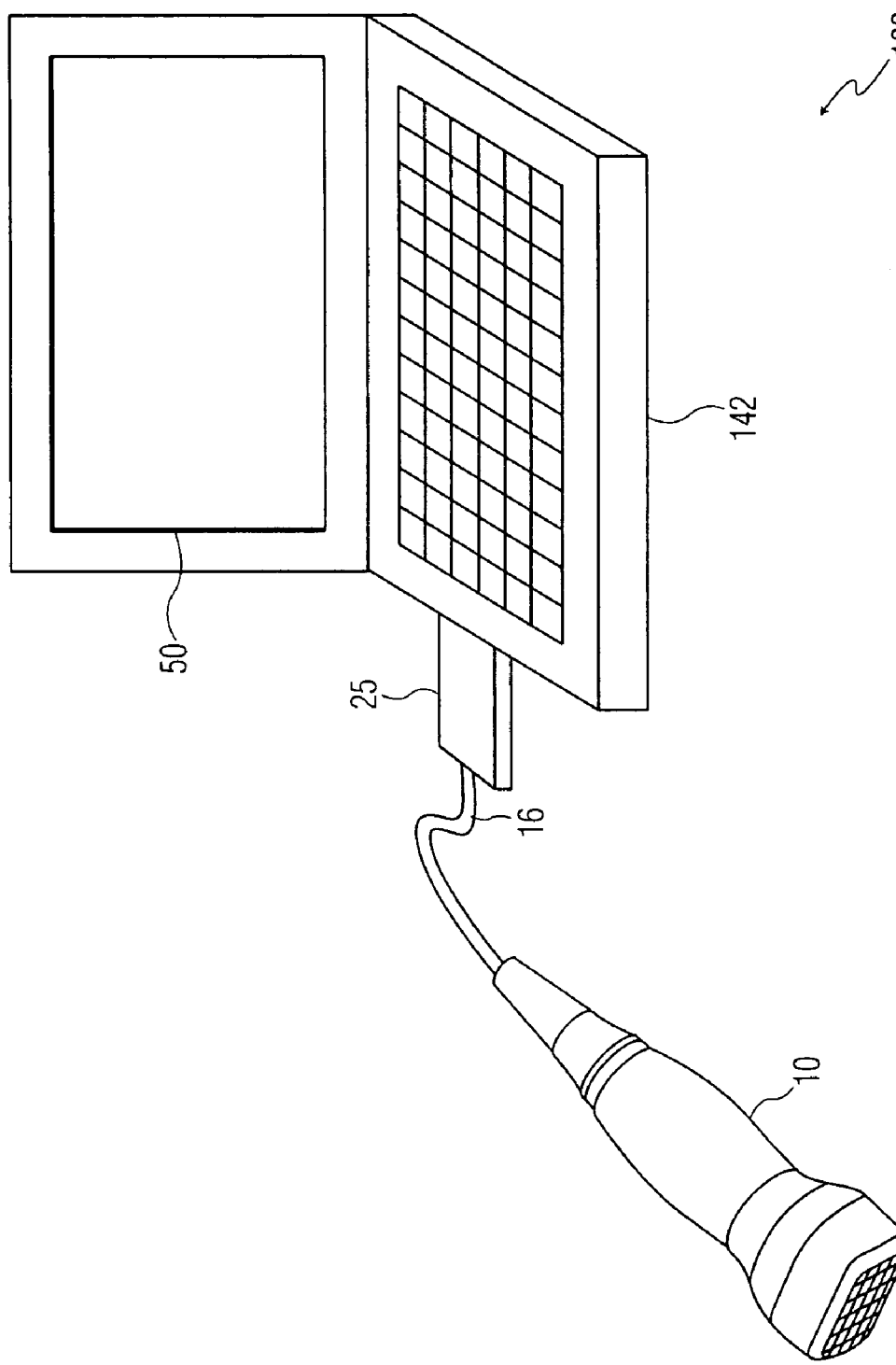
FIG. 6 is a perspective view of the portable ultrasound device of FIG. 1 comprising a laptop computer, according to the present invention.

FIG. 6 is a perspective view of the portable 3D ultrasound device 100 comprising a laptop computer 142. The PC card 25 is inserted into the laptop computer 142 to assemble the system. PC card 25 provides dynamic beamforming and image detection. The CPU, main memory, and an executable program (not shown) of the laptop computer 142 provides scan conversion and rendering, and the display unit 50 is the screen of the laptop computer 142. Thus, the portable 3D ultrasound device 100 of FIG. 6 weighs only approximately 10 lbs.

Figure 7A:
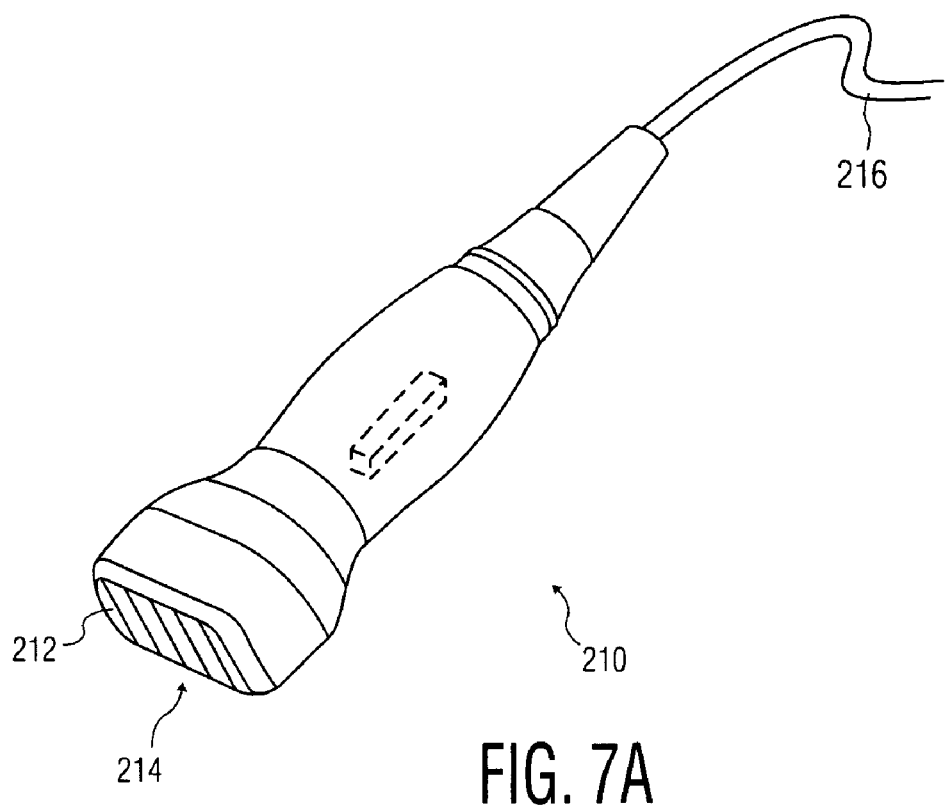
FIG. 7A is a perspective view of a transducer according to another embodiment of the present invention.
Figure 7B:
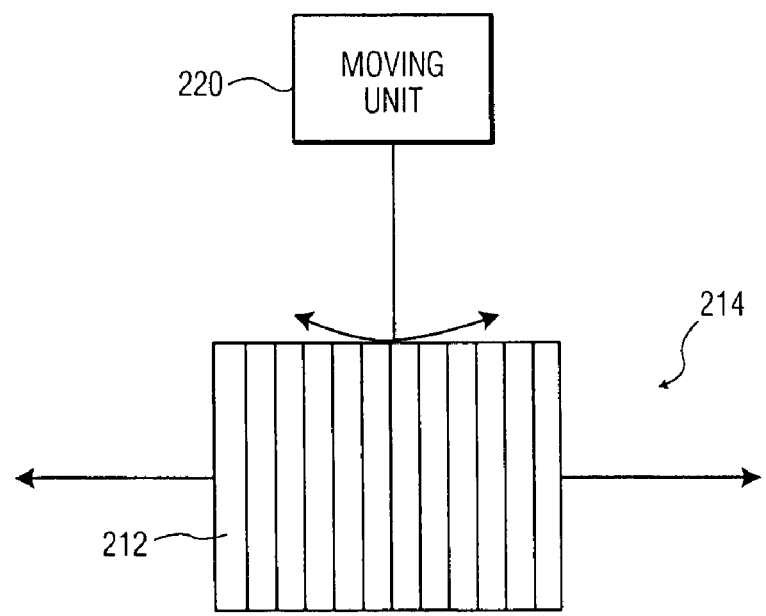
FIG. 7B is a top view of the 1D array of FIG. 7A, according to the present invention.

FIG. 7A is a perspective view of a transducer 210 according to another embodiment of the present invention. The transducer 210 comprises a plurality of acoustic elements 212 arranged in a 1D array 214. FIG. 7B is a top view of the 1D array 214 of FIG. 7A, which comprises approximately 100 of the acoustic elements 212. The 1D array 214 is a linear series of rectangular elements, capable of forming scan beams in only a limited set of angles in a single 2D plane. Thus it must be rotated or rocked by a moving unit 220 in order to generate the multiplicity of slices at different angles that comprise the 3D image. The transducer 210 also comprises a probe cable 216. Unlike previous designs that used a 1D array, or linearly arranged series of elements, to produce a 2D ultrasound image display, the present invention is capable of generating a 3D ultrasound image in a portable or handheld apparatus because of the present use of a 1D array with mechanical array movement combined with improved rendering algorithms and more powerful computers, as described above.

Figure 8:
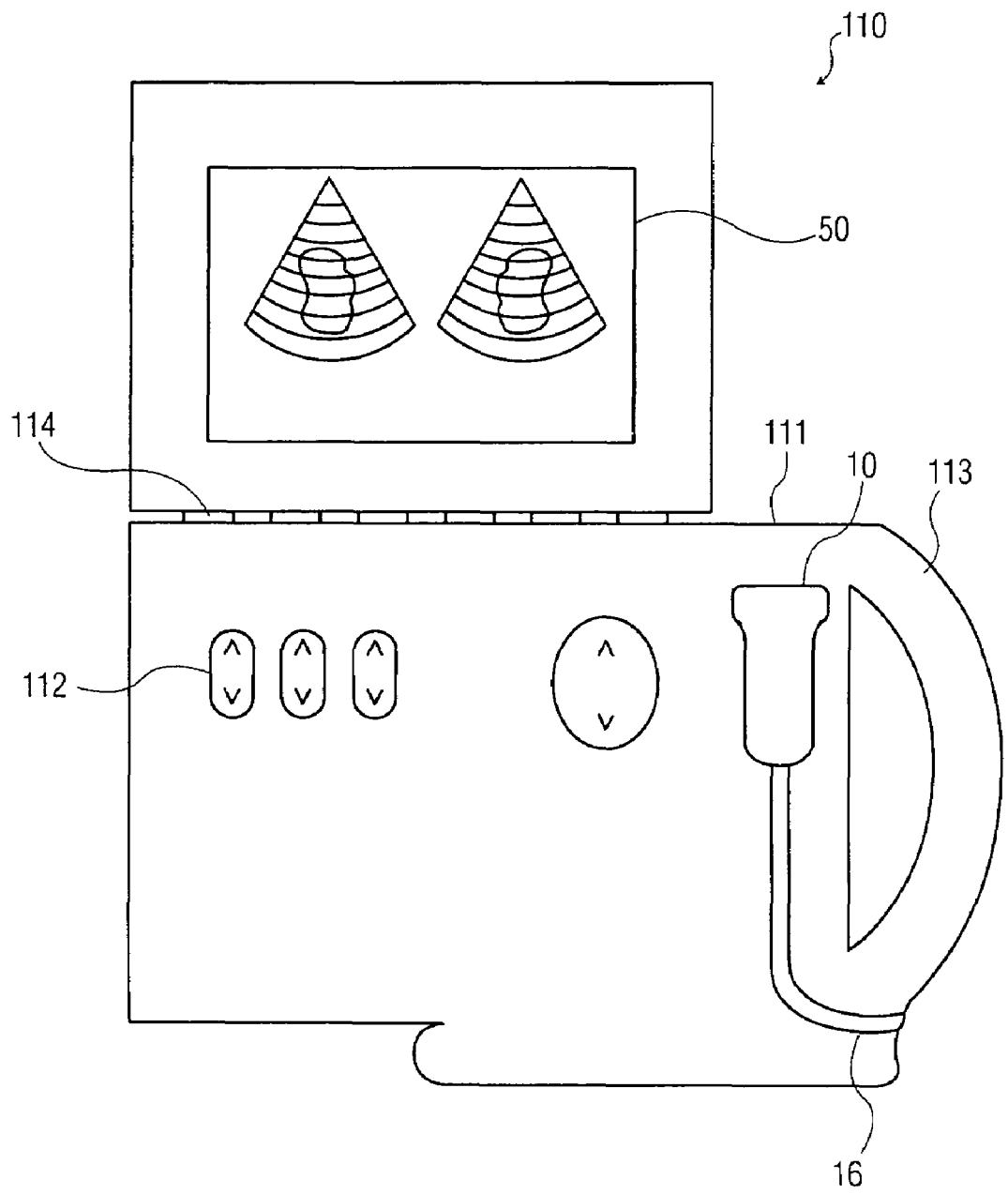
FIG. 8 is a schematic diagram of a hand-held 3D ultrasound device according to the present invention.

FIG. 8 is a schematic diagram of a hand-held 3D ultrasound device 110 according to the present invention. The hand-held 3D ultrasound device 110 is similar in appearance and use to hand-held video recording devices. The dynamic beamformer 20, image detector 30 and scan converter 40 are located within the hand-held 3D ultrasound device 110, and therefore are not shown. The transducer 10 can be stored on a main unit 111 of the hand-held 3D ultrasound device 110 when not in use, and may be removed from the main unit 111 for use on a patient. A handle 113 facilitates transportation and holding of the hand-held 3D ultrasound device 110, and controls 112 are used to adjust the image, which is a bi-plane image in FIG. 8. A hinge 114 allows the hand-held 3D ultrasound device 110 to be closed when not in use, thereby increasing portability.

Figure 9:
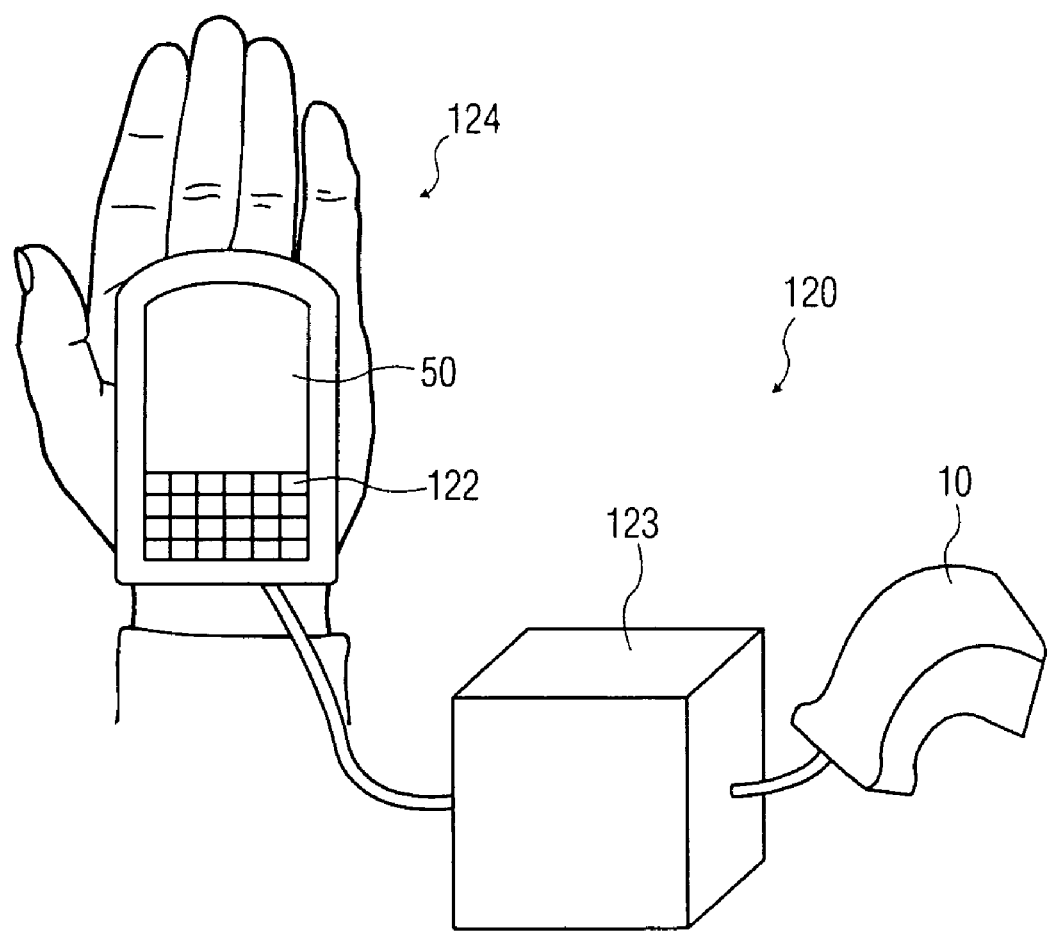
FIG. 9 is a schematic diagram of a portable 3D ultrasound device comprising a handheld PC, according to the present invention.

FIG. 9 is a schematic diagram of a portable 3D ultrasound device 120 comprising a hand-held PC 124. The hand-held PC 124 comprises the display unit 50 and buttons 122 to adjust the image, and performs image detection, scan conversion, and rendering. A battery pack 123 supplies power to the hand-held PC, 124 and may also contain the circuitry to perform image detection. The hand-held PC 124 may be of the type referred to commercially as a PDA, or "Personal Digital Assistant".

Figure 10:
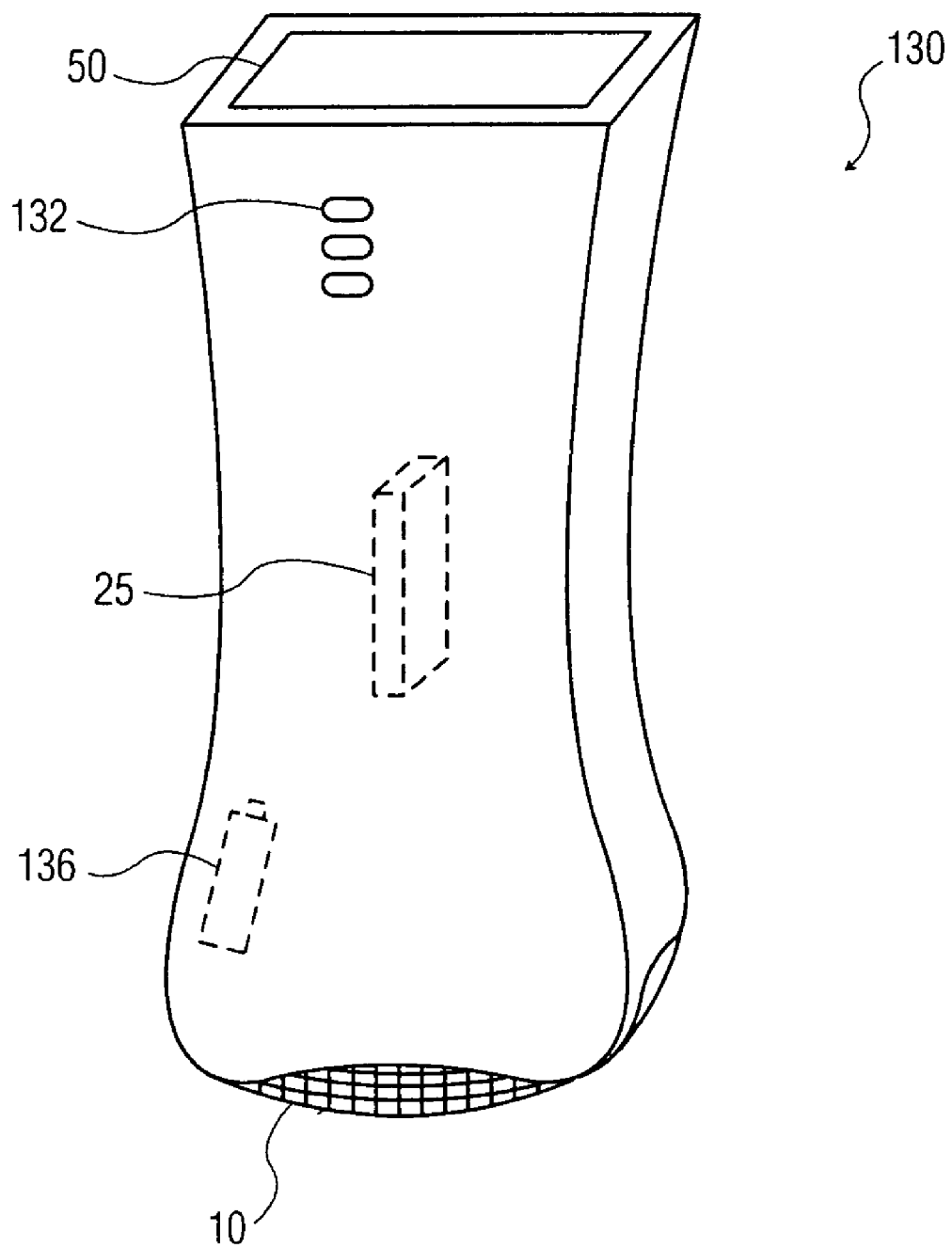
FIG. 10 is a schematic diagram of a portable 3D ultrasound device using a uni-body instrument design, according to the present invention.

FIG. 10 is a schematic diagram of a portable 3D ultrasound device 130 using a uni-body design. In the self contained, uni-body design, all of the elements are contained in a single unit, which includes a battery 136 and control buttons 132.

The present invention provides a truly portable 3D ultrasound device that may be easily carried and used by hand and used at any location. Due to the present use of an improved transducer design, improved rendering algorithms, and more powerful computer capability, the present invention overcomes the limitations of the previous designs.

Although a few preferred embodiments of the present invention have been shown and described, it will be appreciated by those skilled in the art that changes may be made in these embodiments without departing from the principles and sprit of the invention, scope of which is defined in the claims and their equivalents.

What is claimed is:

1. A portable 3D ultrasound device, comprising:
    A. an ultrasound transducer, comprising:
        a transducer array comprising a plurality of transducer elements arranged in a plurality of dimensions, the transducer array including an emitter to emit ultrasound energy and a receiver to receive responses generated in accordance with the emitted ultrasound energy; and
        a plurality of sub-array beamformers, comprising:
            a static receive delay to delay a plurality of the generated responses; and
            a first summer electrically coupled to the static receive delay to sum the plurality of the delayed generated responses to generate a summed acoustic signal;
    B. a signal processor electrically coupled to the first summer to convert the generated summed acoustic signal into a 3D ultrasound image; and
    C. a display unit to display the 3D ultrasound image.

2. The portable 3D ultrasound device of claim 1, wherein the signal processor comprises:
    a generator to generate 3D detected data from the summed acoustic signal; and
    a scan converter to convert the 3D detected data into the 3D ultrasound image.

3. The portable 3D ultrasound device of claim 2, wherein the scan converter and the display unit are contained in a single unit.

4. The portable 3D ultrasound device of claim 2, wherein the signal processor and the display unit comprise a laptop computer.

5. The portable 3D ultrasound device of claim 2, further comprising a battery to power the portable ultrasound device.

6. The portable 3D ultrasound device of claim 2, wherein the signal processor comprises a handheld computer.

7. The portable 3D ultrasound device of claim 2, wherein the generator comprises a dynamic beamformer, comprising:
- a plurality of dynamic receive delays to delay the summed acoustic signals; and
- a second summer electrically coupled to the dynamic receive delays to sum the delayed summed acoustic signals to generate an array of beamformed data.

8. The portable 3D ultrasound device of claim 7, wherein the generator further comprises an image detector electrically coupled to the second summer to receive the array of beamformed data and generate the 3D detected data therefrom.

9. The portable 3D ultrasound device of claim 8, wherein the dynamic beamformer and the image detector comprise a PC card.

10. The portable 3D ultrasound device of claim 1, wherein the portable ultrasound device weighs less than 10 pounds.

11. The portable 3D ultrasound device of claim 1, further comprising a moving unit to move the transducer along an axis.

12. The portable 3D ultrasound device of claim 1, wherein the display unit displays the 3D ultrasound image in real time.

13. The portable 3D ultrasound device of claim 1, wherein the 3D ultrasound image is one of a bi-plane image, a multiplane image, a single image at a user-defined orientation, a volumetric image and a holographic image.

14. A portable 3D ultrasound device, comprising:
- A. a transducer, comprising:
  - a plurality of acoustic elements in a form of a matrix array constructed from a plurality of transducer elements arranged in a plurality of dimensions, the matrix array included to transmit ultrasound energy and receive responses generated in accordance with the ultrasound energy, and
  - a plurality of sub-array beamformers to generate a plurality of sub-array summed acoustic signals from the generated responses;
- B. a dynamic beamformer, comprising:
  - a plurality of dynamic receive delays to delay the sub-array summed acoustic signals, and
  - a full-array summer to sum the delayed sub-array summed acoustic signals to generate a full set of beamformed data;
- C. an image detector to generate 3D detected data from the full set of beamformed data;
- D. a scan converter to convert the 3D detected data into a 3D ultrasound image; and
- E. a display unit to display the 3D ultrasound image.

15. The portable 3D ultrasound device of claim 14, wherein the sub-array beamformers comprise:
- a set of static transmit delays to delay the transmitted ultrasound energy;
- a set of static receive delays to delay the generated responses; and
- a sub-array summer to sum the statically delayed generated responses to generate the plurality of sub-array summed acoustic signals.

16. The portable 3D ultrasound device of claim 15, wherein the 3D detected data comprises a plurality of scan lines in three dimensions, and the static transmit delays focus the transmitted ultrasound energy to generate the plurality of scan lines in three dimensions.

17. The portable 3D ultrasound device of claim 15, wherein the 3D detected data comprises a plurality of scan lines in three dimensions, and the dynamic receive delays focus the received responses to generate the plurality of scan lines in three dimensions.

18. A 3D ultrasound imaging method, comprising the steps of:
- scanning a body with a portable or hand-held device by transmitting ultrasound energy from the portable or hand-held device and receiving responses generated in accordance with the transmitted ultrasound energy with the portable or hand-held device;
- generating a plurality of sub-array summed RF acoustic signals using static beamforming techniques;
- generating a full array of beamformed RF data using dynamic beamforming;
- generating image detected data by image detecting the full array of generated beamformed RF data;
- converting the image detected data to a 3D ultrasound image with the portable or hand-held device; and
- displaying the 3D ultrasound image on the portable or hand-held device.

19. The method of claim 18, wherein the static beamforming techniques utilized in the step of generating a plurality of sub-array summed RF data includes
- delaying the generated responses, and
- summing the delayed generated responses to generate a plurality of summed signals; and wherein the dynamically beamforming the summed signals utilized in the step of generating a full array of beamformed RF data includes:
- dynamically delaying the summed signals, and
- summing the delayed summed signals to generate 3D detected data; and scan converting the 3D detected data into the 3D ultrasound image.

* * * * *